US009912979B2

United States Patent
Cohen et al.

(10) Patent No.: US 9,912,979 B2
(45) Date of Patent: Mar. 6, 2018

(54) SYSTEM AND METHOD FOR FLEXIBLE VIDEO CONSTRUCTION

(71) Applicant: Telesofia Medical Ltd., Ramat Gan (IL)

(72) Inventors: Rami Cohen, Tel-Aviv (IL); Tzvi Rotshtein, Rishon Le'Zion (IL); Danny Ben Shitrit, Rishon Le'Zion (IL)

(73) Assignee: Telesofia Medical Ltd., Ramat Gan (IL)

( * ) Notice: Subject to any disclaimer, the term of this patent is extended or adjusted under 35 U.S.C. 154(b) by 0 days.

(21) Appl. No.: 15/619,698

(22) Filed: Jun. 12, 2017

(65) Prior Publication Data

US 2017/0280065 A1   Sep. 28, 2017

Related U.S. Application Data

(63) Continuation of application No. 14/762,820, filed as application No. PCT/IL2014/050085 on Jan. 23, 2014.

(Continued)

(51) Int. Cl.
| | |
|---|---|
| *H04N 21/233* | (2011.01) |
| *H04N 21/236* | (2011.01) |
| *H04N 21/234* | (2011.01) |
| *H04N 21/43* | (2011.01) |
| *H04N 21/434* | (2011.01) |
| *H04N 7/52* | (2011.01) |
| *H04N 7/54* | (2006.01) |
| *H04N 5/04* | (2006.01) |
| *H04N 5/06* | (2006.01) |

(Continued)

(52) U.S. Cl.
CPC ....... *H04N 21/4302* (2013.01); *G06F 19/326* (2013.01); *G11B 27/031* (2013.01); *H04N 5/04* (2013.01); *H04N 5/265* (2013.01); *H04N 5/91* (2013.01); *H04N 7/52* (2013.01); *H04N 21/233* (2013.01); *H04N 21/2335* (2013.01); *H04N 21/2343* (2013.01); *H04N 21/2365* (2013.01); *H04N 21/2668* (2013.01); *H04N 21/4305* (2013.01); *H04N 21/4307* (2013.01); *H04N 21/4343* (2013.01); *H04N 21/4825* (2013.01); *H04N 21/854* (2013.01); *G06F 19/3456* (2013.01)

(58) Field of Classification Search
None
See application file for complete search history.

(56) References Cited

U.S. PATENT DOCUMENTS

| | | | | |
|---|---|---|---|---|
| 2005/0094030 | A1* | 5/2005 | Brelay | H04N 5/04 348/441 |
| 2005/0276282 | A1* | 12/2005 | Wells | H04N 7/56 370/503 |

(Continued)

*Primary Examiner* — Ricky Chin
(74) *Attorney, Agent, or Firm* — Eitan, Mehulal & Sadot

(57) ABSTRACT

System and method for flexible video construction, particularly of a personalized video clip which provides instructions to a viewer with regard to health and wellness. An ordered list of video input files is chained together, to create a single output video file using a chosen container. Timestamp values are tracked, to ensure synchronization of multiple joined clips, optionally using adjustments of the audio channel or the video channel. A video construction server utilizes information from multiple sources, to construct the video clip.

17 Claims, 12 Drawing Sheets

Related U.S. Application Data

(60) Provisional application No. 61/756,040, filed on Jan. 24, 2013.

(51) Int. Cl.
| | |
|---|---|
| *H04N 5/05* | (2006.01) |
| *H04N 21/2365* | (2011.01) |
| *H04N 21/2368* | (2011.01) |
| *H04N 21/854* | (2011.01) |
| *H04N 21/482* | (2011.01) |
| *G11B 27/031* | (2006.01) |
| *H04N 5/265* | (2006.01) |
| *H04N 5/91* | (2006.01) |
| *H04N 21/2668* | (2011.01) |
| *H04N 21/2343* | (2011.01) |
| *G06F 19/00* | (2018.01) |

(56) References Cited

U.S. PATENT DOCUMENTS

| | | | |
|---|---|---|---|
| 2010/0142624 A1* | 6/2010 | Fujita | H04N 21/4307 375/240.25 |
| 2010/0329630 A1* | 12/2010 | Henry | H04N 21/23406 386/201 |
| 2012/0081567 A1* | 4/2012 | Cote | H04N 21/41407 348/222.1 |
| 2013/0279888 A1* | 10/2013 | Zeng | H04N 21/4307 386/357 |
| 2013/0342632 A1* | 12/2013 | Su | H04N 7/147 348/14.01 |
| 2016/0345051 A1* | 11/2016 | Stewart | H04N 21/4104 |

* cited by examiner

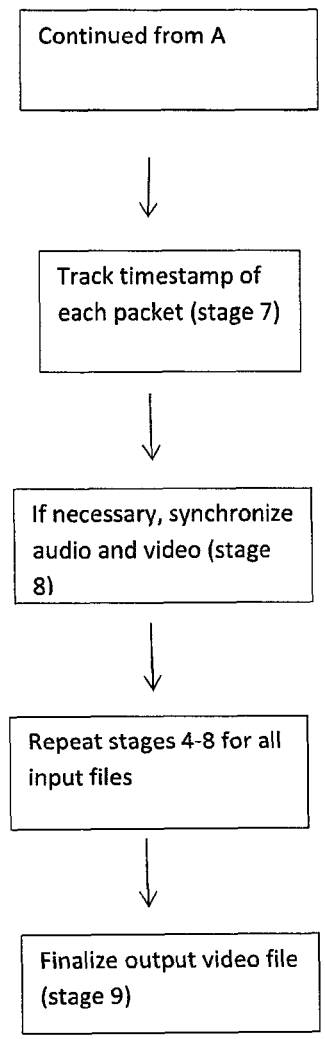
Figure 8 (con't)

SYSTEM AND METHOD FOR FLEXIBLE VIDEO CONSTRUCTION

CROSS-REFERENCE TO RELATED APPLICATIONS

The present application is continuation of U.S. patent application Ser. No. 14/762,820, filed on Jul. 23, 2015, which is hereby incorporated by reference in its entirety; which is a National Stage of PCT International Application Number PCT/IL2014/050085, having an International Filing Date of Jan. 23, 2014, published as International Publication Number WO 2014/115147, which is hereby incorporated by reference in its entirety; and which claims priority and benefit from U.S. provisional patent application No. 61/756,040, filed on Jan. 24, 2013, which is hereby incorporated by reference in its entirety.

FIELD OF THE INVENTION

The present invention relates to a system and method for dynamic and real-time video construction, and in particular, to such flexible construction of a personalized video clip.

BACKGROUND OF THE INVENTION

In a study by Kutner, M. et al. Results From, the 2003 National Assessment of Adult literacy, 2006, incorporated by reference as if fully set forth herein, it was shown that only 12 percent of the more than 19,000 adults surveyed demonstrated what is considered to be Proficient health literacy. This means that 9 out 10 people could not use medical information properly, resulting in incorrect usage of medication, wrong preparation before procedures, misbehavior post-discharge, etc. resulting in poor outcomes. Vernon, J. et al. Low Health Literacy: Implications for National Health Policy, 2007, incorporated by reference as if fully set forth herein, estimated the cost of low health literacy to the U.S. economy in the range of $106 billion to $238 billion annually.

Davis, T. et al. Literacy and Misunderstanding Prescription Drug Labels, 2006, incorporated by reference as if fully set forth herein, found that only 34.7% of patients with low literacy could demonstrate the number of pills to be taken daily for the instruction "Take two tablets by mouth twice daily". Thus the use of written information as the main source of medication counseling for patients is problematic for many. Clearly a need exists to tailor medical instructions to the needs of the specific patient and present it in a way that they will find engaging and memorable.

Personalized instructional videos could provide a potential solution to the above issue and constructing video clips, which are short segments of video data, typically lasting from 30 seconds to 5 minutes or longer, is known in the art. However, currently such construction requires manual intervention, such that personalization of such clips is cost prohibitive. Also, performing this in real-time and on-demand is expensive and currently impossible with low-end hardware. For example, an instructional video clip is usually not personalized to address a specific user, or even the specific needs of a specific user, simply because it is too expensive to do so.

Indeed, personalized on-demand video could find usage in a range of non-medical fields such as advertising, instruction or general informational videos, but the problems described above, such as the time for manual personalization, and the cost of high-end hardware, generally prevents such applications.

SUMMARY OF THE INVENTION

The present invention, in at least some embodiments, overcomes the drawbacks of the background art by enabling automatic construction and personalization of video clips.

According to at least some embodiments of the present invention, there is provided a system and method for automatically constructing personalized video clips. Optionally and preferably, the video clips are instructional video clips, personalized according to at least one instructional requirement of the viewer, in which the viewer is instructed to perform at least one action. While industry acceptable video lengths are between 1.5 minutes to 5 minutes, optionally at least some embodiments are not limited to any video length.

Video is more memorable and effective media than audio or written text, while personalized content is much more effective than generic content when appealing to users, such that this combination is particularly effective for instructional video clips.

According to at least some embodiments, the instructional video clips are constructed for providing medical instructions to a viewer. It should be noted that by "instructional" it is also meant "informational" in that information is imparted to the viewer, optionally even without specific instruction(s) being given. As such the method described herein may optionally be used for any other purpose requiring creation of personalized, real-time and on-demand video clips for example, and without any intention of being limiting, for purposes such as non-medical instruction, advertising, general information, ecards or training.

Optionally and preferably such medical instructions comprises instructing the viewer in the proper administration of a medicament and/or explaining treatments and/or medical operations, more preferably to the viewer him/herself but alternatively to a patient under the care of the viewer. Optionally and most preferably, the personalized instructional video clips are constructed in near real time or real time according to one or more instructional requirements of the viewer. According to at least some embodiments, "near real time" is optionally up to 5 minutes of construction time, and "real-time" is preferably a construction time measured in seconds, optionally less than 2 seconds.

Without wishing to be limited, optionally such personalized instructional medical requirements include one or more of how frequently to take a drug; when to take a drug (timing); whether to take a drug with food, before food or after food; one or more side effects that may occur; one or more side effects that should be reported to a physician. The video may also optionally demonstrate how to receive the drug for administration and may also optionally provide a sketch image of it for easier identification, all personalized for the specific patient.

According to at least some embodiments, the video clip construction may optionally be performed as described below.

Receive viewer parameters, whether from the physician directly or via some EMR/PHR connectivity (or from the viewer), including at least one instructional requirement of the viewer and also preferably one or more types of personal information of the viewer (name, gender and so forth).

Feed those parameters into the Video Script Engine and receive a chain of scenes.

Tailor those appropriate scenes into a single video in real-time.

Optionally produce the video clip in multiple formats applicable to varying display devices; alternatively and optionally, the video clip is only produced in one format.

The video clips are based on health literacy concepts, so they are designed to be clear, concise and easy to understand by passing various text complexity benchmarks; non-limiting examples of such benchmarks include a variety of readability algorithms to estimate the grade level required by the viewer to understand the text, such as: Flesch-Kincaid Reading Ease, Flesch-Kincaid Grade Level, Gunning-Fog Score, Coleman-Liau Index, SMOG Index, Automated Readability Index and so forth.

According to at least some embodiments, the video clip may optionally be performed to the viewer as described below.

1 The physician/pharmacist fills in the prescription details for the customer.

2 The physician/pharmacist sends an email/prints a note providing the link to obtain the video clip, with a code.

3 The customer enters the code through the link.

4 Based on the code the server deduces the set of parameters used to construct the proper video for the patient and then produces the video.

5 The video clip is then displayed to the viewer.

Alternatively, the video clip may optionally be provided to the viewer through a digital media device; for example and without limitation, the physician/pharmacist may optionally prepare a disk on key or other portable digital media storage device at the premises of the physician/pharmacist, through contact with a server as described above.

According to optional embodiments of the invention, the video clip may be converted only to an audio clip, which may optionally be provided to the listener in various formats. For example, the listener may optionally be provided with a code to be used over a phone line, so that the listener is able to listen to the sound track of the video clip.

Such an optional embodiment may optionally be provided by performing a close to real-time extraction of the audio track, then transcoding and delivering it via the phone system, effectively converting the video clip into an audio clip for aural consumption only.

According to at least some embodiments, the audio clip construction and provision to the listener may optionally be performed as described below.

1 The physician/pharmacist fills in die prescription details for the customer.

2 The physician/pharmacist sends an email/prints a note providing the link and a phone number+numeric code.

3 The customer dials that number and is asked to provide the code.

4 Based on the code the server deduces the set of parameters used to construct the proper video for the patient and then produces the video.

5 The server then extracts the sound track from the video.

6 The sound track is converted to a common audio format (such as mp3).

7 The audio is played back to the listener over the phone line.

In a non-medical application the method would preferably be used in a similar way to that described above. For example, in an advertising application:

1 The advertiser provides alternate product messages tailored to specific demographics and also preferably one or more types of personal information of the viewer (name, gender and so forth).

2 The recipients are targeted using advertising tools known in the art such as via Facebook where the name, and age of the recipient is known, and provided with a specific link to view the video clip.

3 Based on the dedicated link the server deduces the set of parameters used to construct the proper video for the viewer and then produces the video including the correct demographic messaging, appropriate actors, animations and theme, and also viewer information.

4 The video clip is then displayed to the viewer in a native video player.

Another example could be a non-medical instructional video;

1 A store selling furniture that requires assembly by the purchaser creates alternative instructional videos based on age and gender groups.

2 The recipients axe provided with a specific link to view the video clip once they complete the purchase at the store. Optionally personal information about the user is obtained during the purchase.

3 Based on the specific link the server deduces the set of parameters used to construct the proper video for the viewer and then produces the video including the correct actors, animations and theme, and also obtained viewer information.

The video clip is then displayed to the viewer in a native video player.

In a similar way the methods described herein can optionally be used for any other purpose requiring creation of personalized, real-time and on-demand video clips.

Unless otherwise defined, all technical and scientific terms used herein have the same meaning as commonly understood by one of ordinary skill in the art to which this invention belongs. The materials, methods, and examples provided herein are illustrative only and not intended to be limiting.

Implementation of the method and system of the present invention involves performing or completing certain selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

Although the present invention is described with regard to a "computer" on a "computer network", it should be noted that optionally any device featuring a data processor and the ability to execute one or more instructions may be described as a computer, including but not limited to any type of personal computer (PC), a server, a cellular telephone, an IP telephone, a smart phone, a PDA (personal digital assistant), or a pager. Any two or more of such devices in communication with each other may optionally comprise a "computer network".

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in order to provide what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DETAILED DESCRIPTION OF THE EMBODIMENTS

The present invention, in at least some embodiments, is of a system and method for automatically constructing personalized video clips. Optionally and preferably, the video clips are instructional video clips, personalized according to at least one instructional requirement of the viewer, in which the viewer is instructed to perform at least one action.

According to at least some embodiments, the instructional video clips are constructed based on the input of a medical professional for providing medical information to a patient viewer. Optionally and preferably such medical information comprises instructing the viewer in the proper administration of a medicament, more preferably to the viewer him/herself but alternatively to a patient under the care of the viewer. Optionally and most preferably, the personalized instructional video clips are constructed in real time according to one or more instructional requirements of the viewer.

According to at least some embodiments, the video clips may optionally be converted to audio only clips, for the user to listen to rather than to view.

Some illustrative embodiments of different exemplary aspects of the present invention are now described in greater detail, for the purpose of description only and without any intention of being limiting. For example, the methods described can optionally and preferably be used to create personalized video clips used for any non-medical, informational, advertising, or training purposes.

Exemplary System—Video Clip Preparation

Figure 1A:
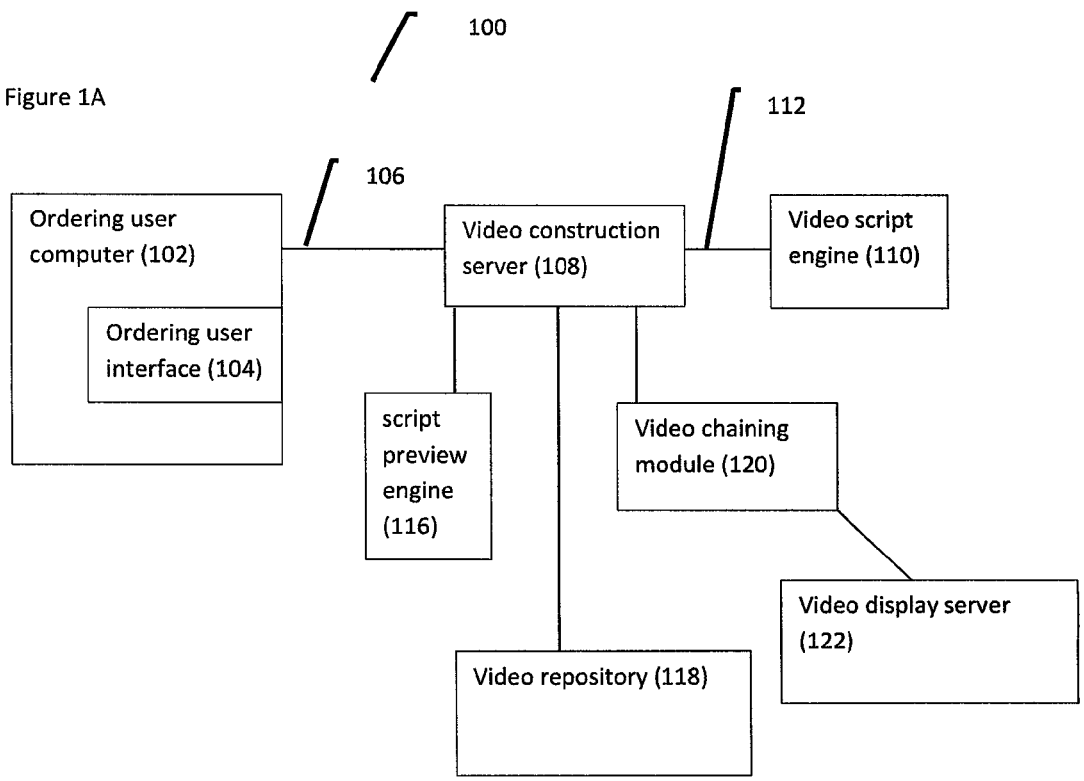
FIG. 1A is a schematic block diagram of an exemplary system for video clip preparation according to an optional embodiment of the present invention.

Turning now to the drawings, FIG. 1A shows an exemplary, illustrative system for video clip preparation according to at least some embodiments of the present invention. As shown, a system 100 features an ordering user computer 102, which operates an ordering user interface 104. Ordering user interface 104 may optionally comprise any software interface, and preferably features a GUI (graphical user interface). For example and without limitation, ordering user interface 104 may optionally comprise a web browser, optionally with a plug-in or other additional software, although this is not required; optionally ordering user interface 104 is implemented as a "zero footprint" configuration through the web browser.

Ordering user computer 102 is in communication with a video construction server 108 through a network 106. Network 106 may optionally comprise any type of computer network, including but not limited to the Internet. Video construction server 108 receives a plurality of recipient parameters from the ordering user through ordering user computer 102. For example, optionally and without limitation, the ordering user preferably enters the name of the recipient and at least one aspect of medical instruction that the recipient is to receive, for example optionally regarding the type of medication that the recipient is to take, although more preferably other parameters are included as previously described.

Video construction server 108 then contacts a video script engine 110, which may optionally be part of video construction server 108 (not shown) but is otherwise in contact with video construction server 108 through a network 112, which may optionally be the same or different from network 106. Network 112 may optionally comprise any type of computer network, including but not limited to the Internet. Video script engine 110 then constructs a script for the construction of the video clip according to the provided parameters and predetermined information that is stored in a database 114, shown as being in direct communication with video script engine 110 but which may optionally be networked.

Video script engine 110 then optionally and preferably transfers the script to video construction server 108, which transfers the script to a script preview engine 116. Alternatively such transfer occurs directly (not shown) between video script engine 110 and scene preview engine 116. Script preview engine 116 then performs an initial construction of the scenes of the video clip, with speech for each portion or scene given as written text. Optionally the written text is added directly to the video clip scenes as an overlay, but optionally and preferably, the written text is converted to verbal speech and is added to the video clips, additionally or alternatively. The conversion of written text to verbal speech is preferably performed automatically without manual interference optionally within the script preview engine 116 as described further below.

Next, video construction server 108 retrieves video information from a video repository 118, which is shown as being in direct communication with video construction server 108 but which alternatively may optionally be networked (not shown). The video data in video repository 118 is optionally and preferably prepared as described in greater detail below. Video construction server 108 then chains the video data together using a video chaining module 120, which again may optionally be implemented through a separate computer (not shown), to construct the video clip.

Once the video clip is ready, it needs to be provided to the recipient, who may optionally be a patient or a family member of a patient. Such provision may optionally be performed through a video display server 122 as shown, or alternatively may optionally be performed by sending the video clip by email, or preloaded onto a portable digital media device and so forth. Video display server 122 may optionally provide a link or other information to video construction server 108, which in turn sends this information directly to the recipient or alternatively to the ordering user through ordering user computer 102; in the latter case, the ordering user would transmit this information to the recipient, again optionally by sending a link to the recipient (not shown). The video may optionally be embedded in a webpage on a website associated with the ordering user such as the website of a hospital or medical practice. Optionally the embedded video is served from the video server 122.

Optionally, ordering user computer 102 may actually comprise a telephone or even a manually written note by the physician, pharmacist or optionally information may be received via some EMR (electronic medical record)/PHR (personal health record) connectivity, the patient themselves or other ordering user (not shown). Regardless of how the ordering user actually places the order, video construction server 108 optionally and preferably receives the above described information, whether from the ordering user or alternatively from another source (not shown).

Figure 1B:
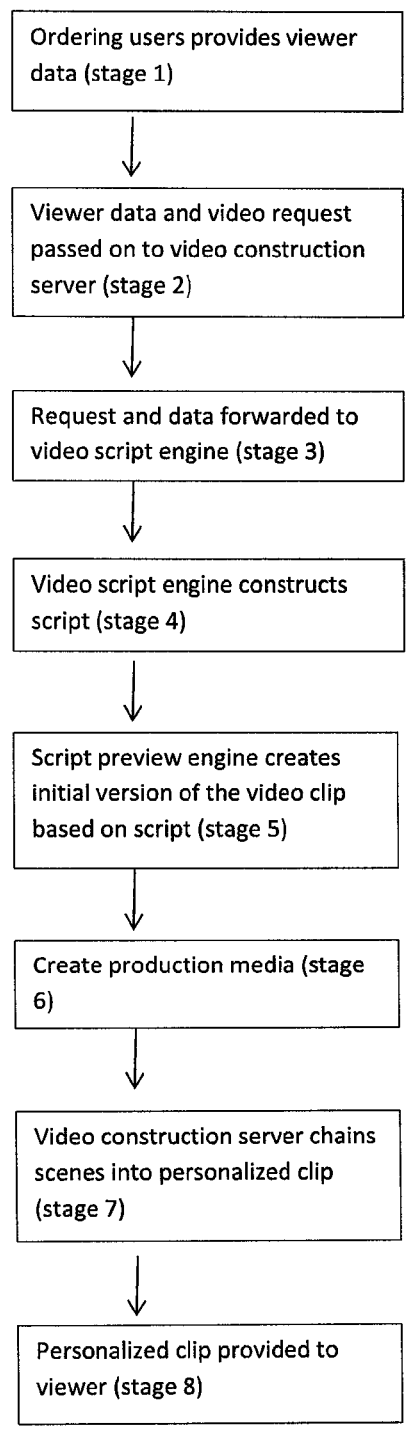
FIG. 1B is a flowchart of an illustrative method for creation of personalized, real-time and on-demand video clips based on the system of FIG. 1A, according to an optional embodiment of the present invention.

FIG. 1B is a flowchart of an illustrative method for creation of personalized, real-time and on-demand video clips based on the system of FIG. 1A, according to an optional embodiment of the present invention. As described in the summary above, a patient who has been prescribed a medication is preferably provided with a personalized video clip illustrating the correct usage of the medication, additional heath guidelines, as well as potential side effects.

In stage 1, an ordering user such as a physician, pharmacist, or other medical professional accesses the ordering user interface 104 on ordering user computer 102. Ordering user provides details of the patient who is to receive the instructional video hereinafter referred to as the viewer. These details optionally include the gender, age, and name, as well as other parameters such as for example, pregnancy status and optionally, at least one aspect of medical instruction that the viewer is to receive, such as the type of medication that the viewer is to take.

In stage 2 the video request and provided information is preferably passed on to video construction server 108 which, in stage 3, passes on the request and data to video script engine 110.

In stage 4, video script engine 110 preferably constructs a script that forms the basis of the video clip based on the provided parameters and predetermined information. This script preferably defines the flow of the video clip and the types of clips to include such as clips with the correct gender and age of the presenter, clips with relevant medication information, and clips showing the specific medication. The script is thus a dynamic/variable script and the final video clip will vary based on the input parameters. Software tools are preferably provided for a script editing user to view and manipulate the flow created by video script engine as will be described further below.

Video script engine 110 preferably provides the created script to video construction server 108 or to script preview engine 116.

In stage 5 script preview engine 116 creates an initial version of the video clip based on the script. This initial version may be lacking the required production media of the final clip such as human actors or animation sequences, but preferably includes video placeholders with the text to be spoken written out on screen or converted to speech by a text to speech engine.

In optional stage 6, the missing production media is produced in a production environment such as a film studio or animation studio for inclusion in the final video clip. This production media optionally including multiple scenes of actors and actresses of varying ages and genders as well as animations of uses and effects of medication, is preferably stored in a repository 118. Preferably, production media also includes a visualization of the medication itself. This may either be sourced from an online database, the medication manufacturer, or generated using a 3D animation tool based on its description.

Preferably multiple copies of all media are stored in the repository with each copy using a different specific encoding standard so that media with similar encoding can be chained together/concatenated within an audio-video container without necessitating re-encoding.

Stages 5 to 6 may optionally be skipped if video script engine 110 already has a defined script for the target viewer and if all necessary production media already exists in repository 118.

In stage 7, in response to the request to view the video clip, video construction server 108 extracts completed scenes from repository 118 based on the script from video script engine 110 and chains these scenes together to form the required personalized video clip using video chaining module 120.

The request to view the video clip may optionally come from the ordering user who may then optionally save the generated clip to give to the patient using removable media or email or a link to download in stage 8. Alternatively the request may come from the viewer who has been provided with a link to view the video clip. In this case the video will preferably be generated on demand.

Video Script Engine

Figure 2A:
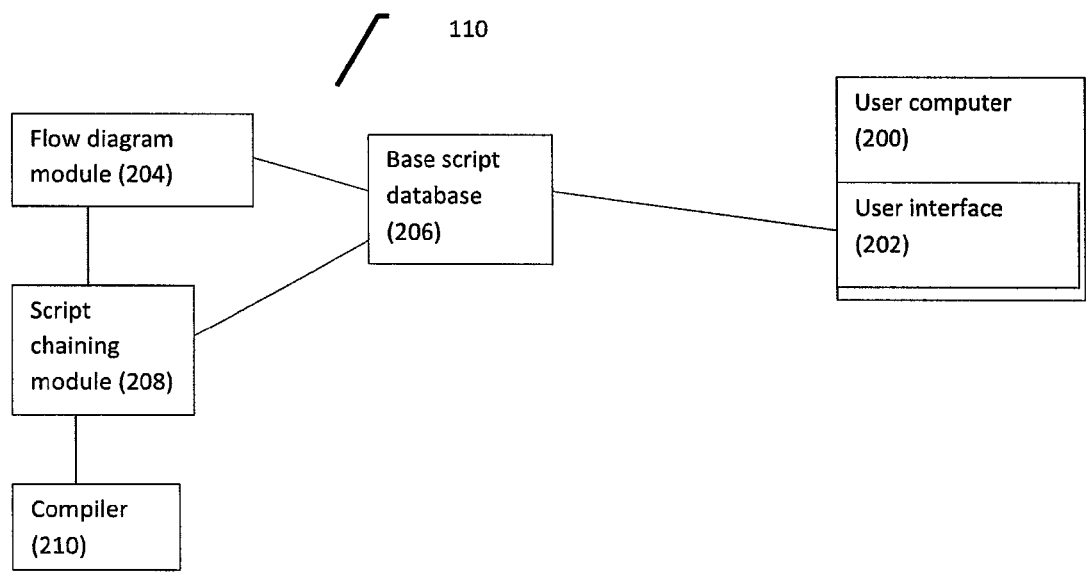
FIG. 2A is a schematic block diagram of exemplary components of a video script engine according to an optional embodiment of the present invention.
Figure 2B:
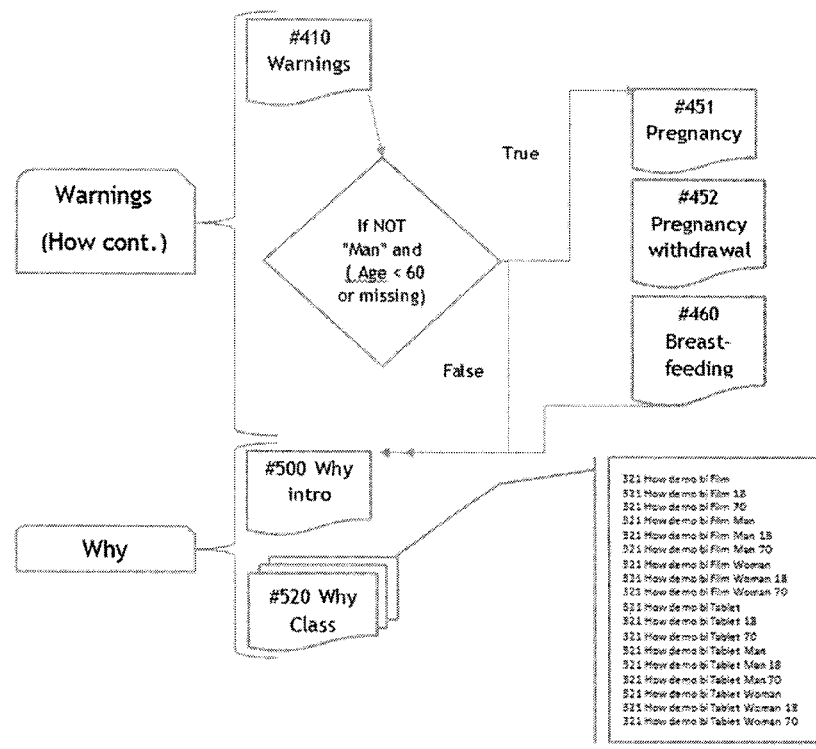
FIG. 2B is an exemplary script diagram produced by the video script engine according to an optional embodiment of the present invention.

As previously described, the dynamic screenplay is constructed by video script engine 110, which is now described in more detail and which is able to dynamically construct a sequential script from a super-set of scripts in an easy manner. FIG. 2a relates to an exemplary, illustrative schematic block diagram of some components of video script engine 110, FIG. 2b shows an exemplary script diagram produced by the script engine, and FIG. 3 relates to an exemplary, illustrative method for operation of video script engine 110.

As shown in FIG. 2a, video script engine 110 is in contact with a user computer 200, which operates a user interface 202. The "user" for this FIG. is the person or persons responsible for making any changes to a script or other components to be input to video script engine 110. User interface 202 may optionally be a thin client or even a "zero footprint" interface, and may optionally be provided through a web browser as previously described. User interface 202 may optionally support the following functions:

Visually display a flow diagram of the script.
Review each and every possible scene combination,
High-level overview showing a list of scenes to evaluate which scene combinations have videos already associated with them.
Generate output that can be used with other tools to help, automate and generate the required videos. This output may optionally include material required for production of media such as text prompts for display on a computer, or a file containing the text prompts for display on a commercial teleprompter, or scene information for display on an action board.
An image thumbnail from the center of the video taken as an icon to visually indicate the scene's contents.

Video script engine 110 preferably comprises a flow diagram module 204, for determining the flow between scenes, according to input parameters received about the recipient, as previously described with regard to FIGS. 1A and 1B. Flow diagram module 204 produces a script in a script definition language. Flow diagram module 204 also preferably receives base script information from a base script database 206. The base script can be any existing script that can be used as the basis and then customized to match the target user or situation. The user may optionally select which scenes may be chained together, or place any other restrictions on determination of the script, from user interface 202. Base script database 206 also preferably includes information about script branching, for example indicating how a script should branch according to received information about the recipient; whether certain scenes should be skipped, and whether certain scenes should be looped (for example, to have the same information and/or request of the patient presented during different parts of the video clip; an example of the latter relates to repeated physical exercises for patients). Such script branching and/or scene skipping may optionally be determined conditionally within flow diagram module 204, according to received information about the recipient.

Base script database 206 optionally and preferably receives a plurality of parameters in advance, before the identity of the recipient is known, in order for production to occur. These parameters preferably have restricted values; for example, with regard to gender; [male, female, unknown], although it is not known what value the user will provide, however the gender parameter must have one of these three values. Base script database 206 preferably contains such information in the format of the script definition language, more preferably in the form of a superscript.

Once the script has been diagrammed by flow diagram module 204, as illustrated by the exemplary script diagram in FIG. 2b, a script chaining module 208 chains the scenes together. Optionally, if multiple drugs have similar scripts, but with slightly different scenes, then the differences may optionally be determined at flow diagram module 204, by making slightly different selections. Script chaining module 208 then prepares the script from the slightly different selected scenes, optionally and preferably storing the scene information in a machine readable format such as XML/JSON.

After script chaining module 208 has prepared the script, the script is optionally and preferably compiled by a compiler 210 into a native script language, which enables both high performance and easy code extension (although it should be noted that native language does not imply native machine code).

Figure 3:
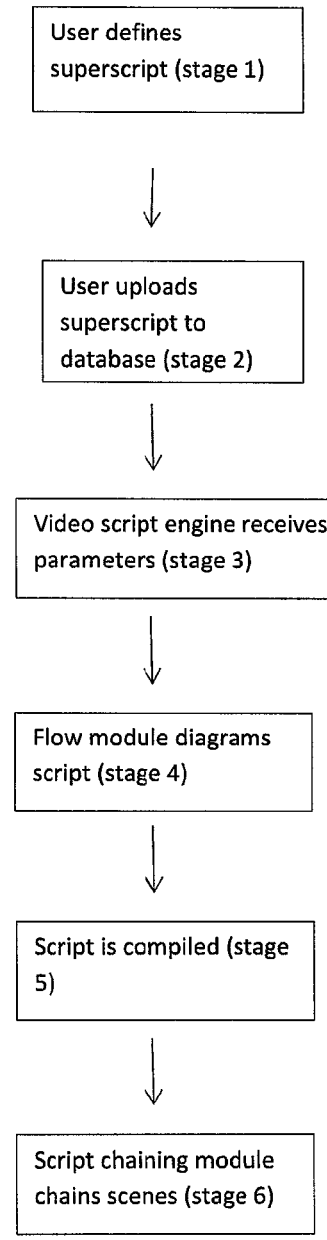
FIG. 3 is a flowchart of an illustrative method for operation of the video script engine according to an optional embodiment of the present invention.

FIG. 3 describes the operation of video script engine 110 in more detail. In stage 1, the user defines a base script and a script flow, through the user interface. The user also defines the parameters that would define its behavior and execution flow. The user also preferably constructs the scenes and conditional branches for a superscript, as illustrated by the exemplary script diagram of FIG. 2b, which is then provided in the base script information database. The conditional branches are also assigned conditions for flow branching, based upon received or calculated parameters by the user, in stage 2, the user uploads the superscript to the base script information database. Stages 1 and 2 occur during preparation for production, that is, before a specific recipient has been identified.

In stage 3, the video script engine receives parameters about a specific recipient for which a script is to be produced. In stage 4, the flow diagram module uses the received parameters and information from the base script information database, including the superscript and other information, to diagram the script.

In stage 5 the script is optionally and preferably compiled by the compiler into a native script language, as described above, which enables both high performance and easy code extension.

In stage 6, the script chaining module then chains the scenes together to prepare the script from the flow diagram. The scenes are then chained together using links. A link has a direction, leading from one scene to another. Each link can optionally have an associated condition that depends on the external parameters. For example, a specific link will be followed only if "the person is over 60".

If multiple links lead from a specific scene, then their conditions must be mutually exclusive (so that at run-time, only one link may be followed).

These scenes, along with all of their variations are then filmed or produced digitally in a studio. This content is herein referred to as production media and optionally includes scenes featuring actors, animated videos, and audio. The system preferably provides tools and aids to assist in the content production, optionally including text for teleprompt devices, scene information for action boards, or scene listings in a format allowing interface to any studio management production tools. Eventually, each scene variation (its variations depend on its dependent parameters) is attached to each video clip produced at the earlier stage. The script is a graph connecting all the scenes and links.

Scene Preview

As previously described, the script preview engine receives the script, directly or indirectly, from the video script engine. In order to analyze the videos, their length and to easily observe the video clips without actually recording them, first, script preview engine uses a TTS (Text To Speech) software to render full length videos, showing the text and speaking it. Such a process may optionally be performed before or during production, or after a specific recipient has been identified. Preferably the process is performed before the actual production media is created (filming/recording) in order to ensure that the scenes play well together (for example that the sentences connect properly), and that the scene/entire-video is not too long/short. Optionally production media may replace/overwrite these automatically generated clips.

This allows seeing the whole video, deducing its length and spotting issues more easily, which might be difficult in any other way.

Figure 4:
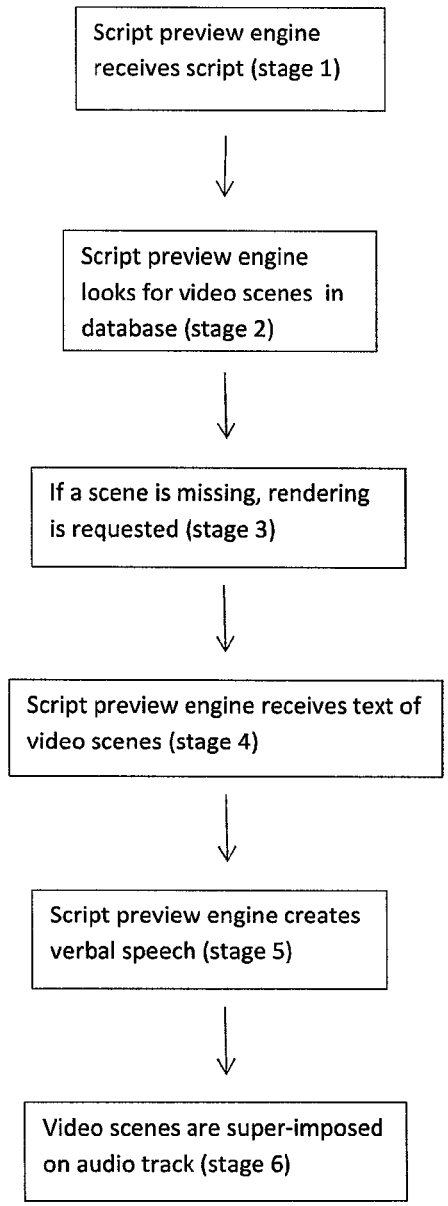
FIG. 4 is a flowchart of an illustrative method for operation of the script preview engine according to an optional embodiment of the present invention.
Figure 5:
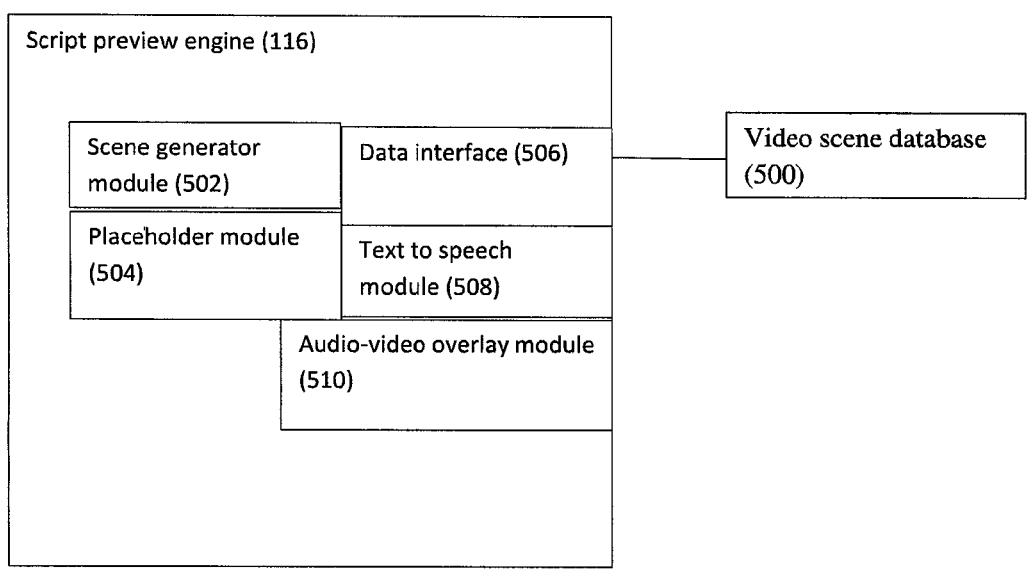
FIG. 5 is a schematic block diagram of an exemplary script preview engine according to an optional embodiment of the present invention.

FIG. 4 describes the operation of script preview engine in more detail, while FIG. 5 shows the components of script preview engine according to at least some embodiments of the present invention (script preview engine has reference number 116 in FIG. 5). In stage 1, the script preview engine receives the script from the video script engine (not shown, see FIG. 1A). In stage 2, the script preview engine looks for video scenes in the video scene database according to the requirements of the script, shown as a video scene database 500 of FIG. 5. Optionally and preferably, video scene database 500 interacts with the script preview engine through a data interface 506, as shown in FIG. 5.

In stage 3, if the script preview engine determines that a scene is missing, it requests rendering of the video data for that scene from video construction server 108 (not shown, see FIG. 1A). Script preview engine 116 generates all the scenes and their variations (for example, dependency on gender) with a scene generator module 502 as shown in FIG. 5. Script preview engine then checks whether production media already exists; if not, it will produce the "place holder" video clip as described above through a place holder module 504 as shown in FIG. 5.

In stage 4, the script preview engine receives the text associated with all of the video scenes from video construction server 108 (not shown, see FIG. 1A) through data interface 506. The scene's text is preferably defined when the scene is written (it may optionally be parameterized based on the input parameters, such as age/gender, so that it looks different depending on them, as described above). The production media is recorded based on that text (a process which occurs offline, without the script preview engine).

In stage 5, the script preview engine 116 creates verbal speech, using a text to speech engine, as is known in the art, with a text to speech module 508 as shown in FIG. 5. Optionally and preferably, the written text is retained, for example to optionally provide closed captioning of the video clip. The verbal speech is placed in an audio file. In stage 6, the video scenes are then super-imposed on the audio track to create a new video clip in full length (as if the video had actually been recorded in one piece, audio and video together) by an audio-video overlay module 510 as shown in FIG. 5. Optionally video/audio synchronization is performed as described below with reference to FIG. 8.

Optionally, if new production media is uploaded by the editor, it will supersede the automatically generated "place holder" video. Such "place-holder" videos contain the scene's text visible in the video and the ITS (automatic computer generated speech) speaking the text. One place holder or production media video is preferably generated per each scene variation (a scene that depends on gender would have two variations, or optionally three variations for "unknown").

Repository Staging

Figure 6:
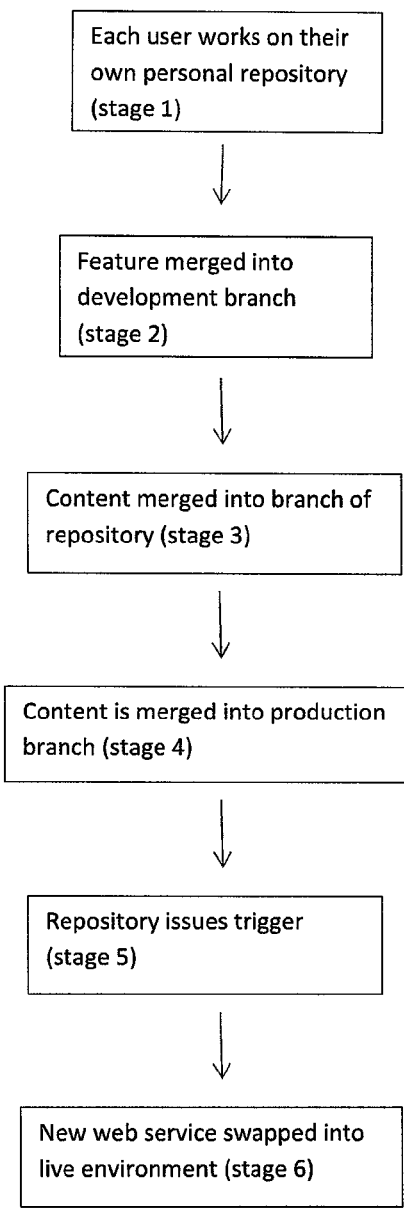
FIG. 6 is a flowchart of an illustrative method for video clip production according to an optional embodiment of the present invention.

FIG. 6 relates to an exemplary method for the production stage, for constructing code so that video clips can be constructed later. Optionally and preferably, the repository is built upon a repository service, such as "git" for example. The production environment is also composed from a repository which is cloned from a local repository. The cloning is automatically triggered when the contents of a specific branch gets updated. This makes getting new web content to production extremely fast and simple.

In stage 1, each user works on their own personal repository to create the code for a scene. As described previously, scenes are the basic-block component for composing a script. These scenes are shot/produced later on in the process.

Each scene is composed from: its text, parameters, shot description and more. Each scene can depend on externally provided parameters (such as: gender, heart condition etc.). Depending on parameters means that a scene can have multiple variations based on the provided input. It can also optionally have different content (text) associated with each variation (for example: for "male" it says "Hello sir" and for "female" it says "Hello ma'am"). Each scene can have additional properties like shooting parameters (director instructions).

As each user completes a feature upon which they are working, in stage 2 that feature is merged into a development branch in the centralized company repository. In stage 3, the content is merged into a particular branch of the repository. Source control tools, such as "git" or "subversion" allow the user to branch (or create a branch) of the user's files so that the user can work on some code without affecting the primary branch, allowing switching back and forth between the two. Next, a trigger is issued and the added content is automatically synchronized to the development web server for testing.

In stage 4, when testing is complete, the content is merged into the production branch in the central repository. In stage 5, the repository issues a trigger that would synchronize the production repository to the production environment into a staging area. It would use the repository's networking and synchronization capabilities to do that so that no data is lost or missed in the process even if the cross network is unreliable.

In stage 6, when the content in the staging area is confirmed to be working properly, an atomic single command is issued to swap the new web service to the live environment, to prevent the problem of partial updates while the data is being synchronized to production.

Scene Production

Figure 7:
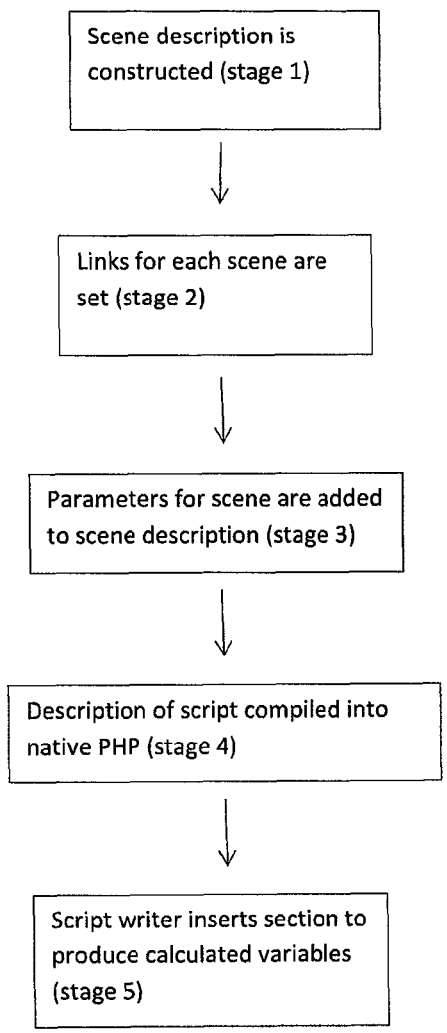
FIG. 7 is a flowchart of an illustrative method for video scene production according to an optional embodiment of the present invention.

FIG. 7 relates to an exemplary method for scene production, including creation of a superscript (that allows for different variations in the scene). In stage 1, the scene description is constructed (for example, optionally manually by a user as previously described). The description contains the scene's name, the scene's text (i.e. "Hello, I am Dr. House" . . . ") which can contain multiple variations if the scene depends on external parameters such as age.

For example, the scene may contain a different text for each age variation: "Hi, I see you're a young and healthy person" or "- "Hi, I see you're an elderly and distinguished person". The scene description may also optionally include one or more calculated variables to permit scene variation more simply using just one text instance; for example: "Hi, I see you're $welcome allow me to explain . . . "

The variable $welcome is pre-calculated when the script starts its evaluation by using the value of the $age parameter (variables are essentially extensions of the parameters the script receives). The scene description also contains the parameters it depends upon. In the example above it would be $age.

The scene description contains director instructions (such as close-up, mid-shot, animation, etc.). Below is a non-limiting example of scene description in XML, although other languages may optionally be used as previously described, such as JSQN for example.

```
<scene>
    <name>Welcome $age</name>
    <text>Hi $welcome allow me to explain to you the merits of this
new medication</text>
    <property>close-up</property>
</scene>
```

Optionally and preferably the script is reviewed to make certain that the text's literacy level can be understood by most audiences.

In stage 2, the links for each scene are set. As previously described, each scene can be linked to another via a link, which is preferably also included in the scene description; alternatively, the links may optionally be kept in a separate XML/JSON file than the scene's file for added flexibility and simplicity (the link contains the source & target scenes along with an optional condition). Links have an optional condition associated with them. Optionally conditions may be written in free form (using PHP syntax).

For example, a link leading from the "welcome" scene to the "medication description" scene might not have any condition since the script continues from one scene to the next unconditionally. But it is possible that for a medication warning scene, different warnings may optionally be required for men and women, in which case it is necessary to link to different (and mutually exclusive) scenes.

For example, when proceeding from the "medication description" scene to the "medication warnings" scenes—here an XML description of how such a link would appear.

```
<link>
    <source scene="medication description" />
    <target scene="medication warnings for
    men">$gender="male"</target>
    <target scene="medication warnings for
    women">$gender="female"</target>
    <target scene="medication warnings all" />  <!-- Optional
default target scene if none of the others matched -->
</link>
```

As opposed to conventional movie scripts, this allows creating a dynamic/variable script that will produce different set of scenes based on the parameters it receives.

In stage 3, if not previously determined, the parameters for each scene are added to the scene description. The parameters are provided to the script from the ordering user (the ordering user for example may optionally populate a form and fill in those parameters, such as $age, $gender etc.) they will be fed into the script (dynamic script) and the script will evaluate a linear (sequential) order of scenes that compose the end-video to be displayed for the user.

In stage 4, in order to improve performance and flexibility, the description of the script (in JSON/XML) may optionally be compiled into native PHP as previously described to be run efficiently. In stage 5, optionally before or during such compilation, the script writer may choose to insert a section that can produce calculated variables. Calculated variables are simply parameters which depend on parameters that the ordering user provides.

For example:

$age_group=$age<50?"young":"old";

In this example a new parameter (calculated variable) is added, which is called $age_group, that will contain the words "young" or "old" based on the $age that the user provided as parameters.

This allows simpler conditions and scenes later, since changes can be based on that variable rather than on the $age (that may contain many values).

Each scene has a name which contains the parameters it depends upon. For example a scene called "Welcome $age_group" will have two variants (according to the definition of $age_group above).

There are now two variants called effectively "Welcome young" and "Welcome old". For each variant there may be a different text (so it is necessary to film the actor saying different things) and accordingly, separate video files.

At the end of the process the produced video files are associated with each scene variant, optionally according to one of a number of different processes. For example, this could be accomplished by embedding variables in the text, for example "Hello, I see you're a $gender" (which would become, for men, "Hello, I see you're a male"). Another possibility is to use calculated variables. They are based on the input parameters, for example if $age<30$state="good enough" else $state="can be better" and then use $state as a variable in the text. Another possibility is to allow embedding script code inside the scene's text so this condition above could optionally be embedded directly into the scene's text—and as such it would cause different text to be displayed when the scene's text is evaluated.

Video Tailor

Figure 8:
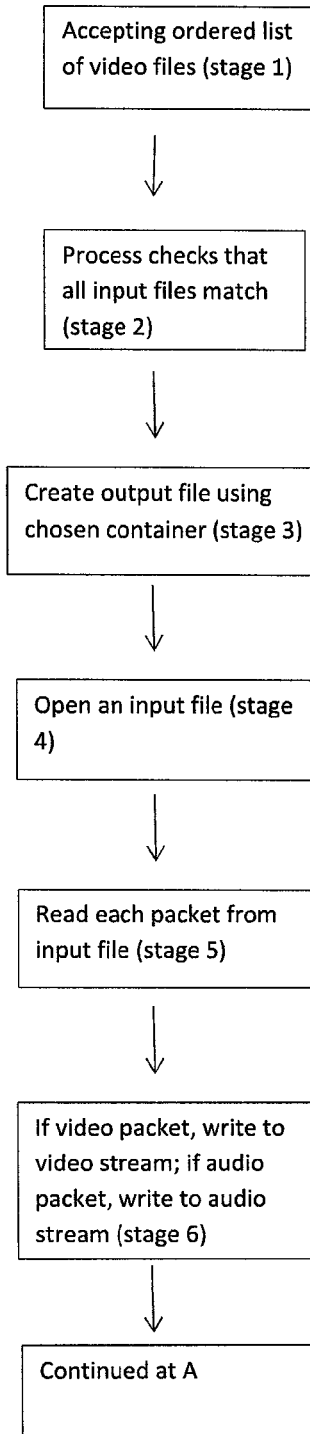
FIG. 8 is a flowchart of an illustrative method for chaining video scenes together according to an optional embodiment of the present invention.

FIG. 8 is an exemplary, illustrative method for chaining video scenes together according to at least some embodiments of the present invention. Chaining may optionally be performed according to any of a number of different methods; however, in order to produce a comprehensive on-the-fly video using commodity hardware and in an efficient manner, without any video quality loss, there is a need to improve the re-transcoding phase needed when chaining the various scenes into a single video stream ready for serving. This is especially true when multiple formats are to be supported (each browser/device has its own preferred video playback formats).

The below method is different from those known in the art for a number of different reasons; without wishing to be limited in any important way, one important difference is that the method eliminates the transcoding phase altogether. Furthermore, the method can chain multiple video files at various formats very rapidly, without specialized hardware, making it suitable both for real time video stitching and also for pre-rendering huge quantities of videos.

This unique technology enables thousands of such real-time tailored videos to be served each day from a single hosted machine. For most video formats, especially those used on web enabled devices, there are no tools for chaining/combining/concatenating video segments without re-transcoding them anew. Re-transcoding has two flaws. The first is that it causes an additional video quality drop and the second is that it requires much CPU resources to accomplish, effectively creating a response delay and reducing the amount of clients that can be served by each machine.

Media files are usually composed from several layers, including a container (aka format), which describes the outer format of the file that contains the video (often matches the file extension's name, such as .avi .mpg .mp4.wmv etc.). The container encapsulates the streams of data inside it. It is mostly oblivious to the actual content it contains. It defines how the streams are encoded and interleaved.

Each container can have several streams, but the most common use is to have one stream of each: video and audio. The two are interleaved (by the container) so that the audio streams that share a similar playback timestamp would correlate closely within the file.

Codecs are the actual algorithms that compress/encode the data streams (either audio or video) and are stored within distinct streams within the container.

The problem that needed to be solved for this aspect of the present invention was how to combine (chain) multiple video clips into a single video for playback. There are two common approaches to solving this problem. One is to solve it within the client (player) and the other is to solve it within the server. In many ways, it is desirable to chain the video clips together inside the client (player) however that is not always possible especially on Apple devices (iPhone/iPad) unless one builds, submits and maintains a specific application for that.

A more desirable solution would provide a "zero install" approach so that it would work in any modern web browser, such that the video clips would need to be chained at the server side. However, the only tools that are known in the art generally re-encode (meaning, decompress the separate clips, chain them together and re-compress).

This has two undesirable side effects. The first is quality loss (due to the re-compression, since video compression is lossy meaning it drops some information thus reducing quality) and the second is time. Using standard computers to re-encode a 3-5 minutes movie takes too long to permit real-time broadcasting.

This exemplary, non-limiting, illustrative method according to at least some embodiments of the present invention is able to read the encoded data packets from multiple files and chain them together without re-encoding them (as long as the input encoding/format/codec is the same as the output encoding/format/codec). This way there is no re-encoding needed, resulting in faster performance (since the re-encoding takes most of the time) and no quality loss.

According to the specific example of the method described below, and without wishing to be limited in any way, the method was determined such that the output would support the MP4 audio-video container format (with H264 encoding for video and AAC for audio) and WebM (with the VP8 encoding for video and Vorbis for audio), as this would support modern web browsers. Preferably, the video can be played by most modern browsers without installing any application or plugin.

Implementation Details

Optionally, the below process uses the low-level libraries of an open source library called ffmpeg for reading and processing containers; alternatively, other suitable libraries could be used instead.

Turning now to FIG. 8, in stage 1, the process starts by accepting an ordered list of video files that it needs to chain together and a single output video file name. In stage 2, the process checks that all the input files match (meaning they both have the same format, the same streams, the same codec, the same resolution etc.). In stage 3, the process creates the output file using the chosen container (to match the container of the input files). This may optionally be performed through the above described libraries. In stage 4, the process starts opening each of the input files.

In stage 5, each packet is read from the file, preferably without any decoding or processing in order to achieve the desired performance. In stage 6, if the packet is a video packet, it is written to the video stream of the output file as-is. If the packet is an audio packet, it is written to the audio stream of the output file as-is. In stage 7, the timestamp (the DTS & PTS values) for each packet (audio or video) is tracked in order to keep all the streams synchronized after completion of the processing of each input file;

Due to how current video/audio encoders are designed, both the audio frames and video frames generally have different durations that make it difficult to perfectly synchronize the video and audio when joining multiple clips together. In stage 8, the later timestamp (from all the input streams) is selected for resynchronization. This is achieved by adding a quiet audio delay or by postponing the starting video frame for the next input video file in sequence.

Alternatively, when multiple clips are joined, the following method can be used to adjust both the audio and the video channels to have the exact same duration thus ensuring continued synchronization.

1. A calculation is made of an optimal time period based on the source media length, sampling rate, and codec type. The optimal time period will result in a number of complete audio and video frames that start together and end together exactly within the period.
2. The clip is adjusted so that its length conforms to an exact multiple of the optimal period calculated above. Additional frames are preferably removed either manually or preferably using an automated computational method.

For example: In an MP4 container with video encoded using the H264 codec and audio using AAC codec; video is saved at 24 frames per second and audio is sampled at 44,000 samples per second. By default all AAC audio frames have 1024 samples each.

A common synchronization period t would be expressed as follows:

$$t = v\frac{1}{24} = a\frac{1,024}{44,000}$$

Where both "a" and "v" are integer values. In order to work with integers only, a simple algebraic manipulation yields;

$$v \cdot 44,000 = a \cdot 24,576$$

The minimum a & v integers are now determined such that the condition above holds. In this example a=1375 and v=768. To determine the optimal period t, these numbers are inserted into the original equation to obtain a synchronization period of 32 seconds long.

$$t = 768 \cdot \frac{1}{24} = 1,375 \cdot \frac{1,024}{44,000} = 32 \text{ seconds}$$

For this combination of audio and video codecs, these are the number of frames that the clip must be constrained to so that the audio & video are always perfectly synchronized. Preferably, combinations of codecs and frames rates should be chosen that result in short periods that can be easily applied to production media of any length.

Stages 4-8 are repeated for each input file until all have been processed. In stage 9, after the input files have been processed, the output video file is finalized.

Upon testing, the above process was shown to achieve excellent performance (3 minute long video clips, composed from 15 different video scenes, were chained together in under a second).

This process works reliably for many different formats, including without limitation MP4 and WebM formats and potentially other formats as well (as long as the source scenes are prepared in both formats).

The resulting videos are directly playable via any modern browser.

Pill Visualizer

In order to provide comprehensive instructions about medication to be taken by the viewer of the video it is preferable to include an image of the medication and optionally a verbal description. The image of the pill is preferably selected from a database of real photographs and machine generated images. The image is preferably sourced from an official medical source, such as the FDA in the US. Preferably the image data is updated periodically, such as daily, weekly or monthly.

Alternatively, the image of the pill may be sourced from the manufacturer.

Figure 9:
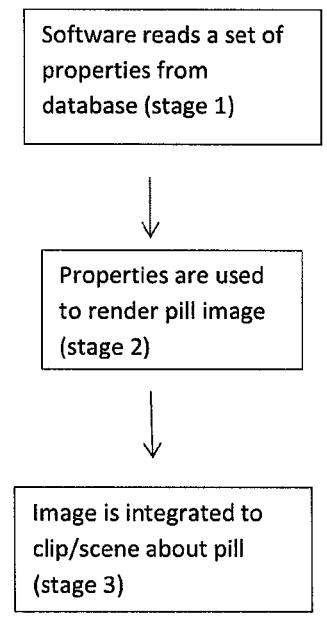
FIG. 9 is a flowchart of an illustrative method for pill visualization according to an optional embodiment of the present invention.

Alternatively, as shown in FIG. 9, there is a non-limiting exemplary method to retrieve pill information from the database and produce an image representing the pill's appearance, based on the varying parameters there (including but not limited to color, shape, imprints).

The method is optionally capable of producing either flat (2 dimensional) or more realistic 3D (ray traced) images of the pill, thus permitting the user to validate that the pill they're taking is indeed the one to which reference is made in the video. Optionally, the method can also be used to create a video.

1 In stage 1, the software reads a set of pill properties such as shape, color, size, score and inscription from the database.

2 In stage 2, these properties are then used to define and render an image of the pill using one of two forms. For example, for drawings, optionally either image drawing routines (to draw a flat image) or a 3D ray tracer engine (such as Povray) are used to produce an image matching the properties of the described pill. Such images may optionally be created even without an actual image of the pill, through an approximation so that the viewer can confirm that they have the proper pill in hand.

a Using 2D methods, resulting in a flat schematic form.

b Using 3D methods, by employing a ray tracer approach the image is rendered with lighting/shadow and realistic looking appearance.

3 The image is then taken and integrated to produce a short video describing the actual pill. Optionally such a video may be produced by rendering the image into a short movie clip along with a sound track describing the pill vocally (for example; 'It's a round blue pill.'). This is done by taking the image and repeating it to make a movie while adding another channel providing the audio describing it.

Data Mining and Analysis

Optionally according to at least some embodiments, there is provided a method for automated data analysis, comprising obtaining data from official medical sources, such as the FDA in the US. Preferably the information is obtained periodically, such as daily, weekly or monthly.

The data is mostly structured (meaning, it was designed to be read/processed by computers in a standard and well defined format) so it is possible to scan, analyze and then convert into a format for a database that can be accessed by the above video construction server.

If the data is not well structured (for example, provided in free text and meant for human consumption), optionally relevant information is extracted by using text processing techniques and/or NLP (natural language processing). This information is then interpreted and loaded into the above database.

This information is then used for automatically producing rich media content, such that the above video clips include up to date information. The information is optionally and preferably loaded and analyzed weekly so that information stays current. Also optionally and preferably, differences between the older and newer data sets are determined to optionally apply some customizations or improvements to the produced videos.

The automated process optionally and preferably features the following stages.

1. Access online or offline data sources on regular intervals and pull the database contents. A non-limiting example for such medical sources of information would be the FDA.
2. Process and filter the contents of the database. Use customized rule-sets to detect invalid content and exclude it.
3. The remaining content is refined by extracting relevant information.
   Structured information is extracted directly whereas unstructured data (such as "free text") is processed and mined using rule-sets and NLP based techniques for relevant information.
4. The extracted information from all the sources is loaded into a database. Next the contents of each source are merged to make the entire data set available easily to the application.
5. The previous database is compared to the new one and the differences are used to evaluate required changes to the videos.

REFERENCES

1. Kutner, M., Greenberg, E., Jin, Y., and Paulsen, C. The Health Literacy of America's Adults: Results From the 2003 National Assessment of Adult Literacy (NCES 2006-483). U.S. Department of Education. Washington, D.C.: National Center for Education Statistics, (2006).
2. Vernon, J. A., Trujilio, A., Rosenbaum, S., & DeBuono, B. Low health literacy: Implications for national health policy. Washington, D.C.: Department of Health Policy, School of Public Health and Health Services, The George Washington University, (2007).
3. Davis, T. et al. Literacy and Misunderstanding Prescription Drug Labels, Ann Intern Med. 145:887-894, (2006).

The present invention has been described and embodiments provided relating to construction of video clips. The present invention is now further described by the claims which follow. Optionally, any of the above embodiments or sub-embodiments described herein may be combined to form any suitable combination or sub-combination.

What is claimed is:

1. A method of video construction by a machine comprising at least a hardware processor, the method comprising:

(a) accepting (I) an ordered list of video input files intended for being chained together, and (II) a single output video file name;

(b) checking that all of said video input files match each other by having same encoding, same format, and same codec;

(c) creating an output file using a chosen container which matches, by its encoding and format and codec, a container of said video input files;

(d) sequentially opening each of said video input files;
(e) reading each packet from each video input file, without packet decoding, wherein each video input file comprises video packets;
(f) if the packet is a video packet, then writing the packet as-is to a video stream of the output file;
(g) if the packet is an audio packet, then writing the packet as-is to an audio stream of the output file;
(h) tracking the DTS timestamp value and the PTS timestamp value of each audio packet and each video packet, to keep all streams synchronized after completion of processing of each video input file;
(i) ensuring continued synchronization of multiple joined video input files by adjusting both the audio and the video to have the exact same duration, by performing one of:
  (A) selecting the later timestamp from all the video input streams for resynchronization, by performing either: (I) adding a quiet audio delay, or (II) postponing the starting video frame for the next video input file;
  (B) calculating an optimal time period based on lengths of the video input files and their sampling rates and codec types; wherein the optimal time period results in a number of complete audio and video frames that start together and end together exactly within said optimal period; and adjusting each video input file so that its length conforms to an exact multiple of the optimal time period as above; and removing additional frames from the video input files either manually or automatically;
wherein step (i) is performed by determining a common synchronization period T for (I) encoded video that is saved at F frames per second, and (II) encoded audio that is sampled at S samples per second, wherein each audio frame has L samples,
wherein the common synchronization period is calculated by using the following equations, $$T=V=1/F=A\times L/S$$

by determining the minimum integer values of parameter A and parameter V such that the following condition holds true:

$$V\times S=A\times F\times L;$$

wherein the method is performed by said machine which comprises at least said hardware processor.

2. The method of claim 1, wherein the video input files are chained into said output file which is one of:
(a) informational video, to provide information to a viewer;
(b) instructional video, personalized according to at least one instructional requirement of the viewer, in which the viewer is instructed to perform at least one action.

3. The method of claim 2, comprising:
constructing the instructional or informational video for conveying information to the viewer;
instructing the viewer in health and wellness, regarding a proper administration of a medicament, through one or more automatically-constructed videos.

4. The method of claim 1, comprising:
based on said common synchronization period T, constraining the number of frames of the output file so that the audio and video are always perfectly synchronized.

5. The method of claim 1, comprising:
choosing combinations of codecs and frame-rates that result in short periods that can be applied to production media of any length.

6. The method of claim 1, comprising:
repeating steps (d) through (i) for each video input file until all said video input files are processed.

7. The method of claim 1, comprising:
constructing code to enable video output files to be constructed at a later stage, by performing:
building a repository upon a repository service, wherein a production environment is composed from a repository which is cloned from a local repository; wherein repository cloning is triggered automatically when the contents of a specific branch is updated.

8. The method of claim 7, wherein each user works on his personal repository to create the code for a scene, wherein each scene is composed from at least: text, parameters, shot description;
wherein each scene can depend on externally provided parameters, such that a scene can have multiple variations based on the provided input;
wherein each scene can optionally have different text content associated with each variation.

9. The method of claim 8,
wherein each user of a plurality of users works on his own personal repository,
wherein the method comprises:
as each user of said plurality of users completes a feature upon which he works, merging said feature into a development branch in a centralized repository;
merging the content into a particular branch of the centralized repository;
automatically synchronizing added content to a development web server for testing;
upon completion of testing, merging the content into a production branch in the centralized repository;
issuing a trigger to synchronize the production branch of the centralized repository into a staging area;
when the content in the staging area is confirmed to be working properly, issuing an atomic single command to swap a new web service to a live environment, to prevent partial updates while data is being synchronized to production.

10. The method of claim 1, comprising:
performing video scene production by creating a superscript that allows for different variations in the video scene; wherein the video scene production comprises:
constructing a scene description, which contains: (I) a name of the scene, and (II) parameters that the scene depends on, and (III) a text of the scene which contains multiple variations if the scene depends on external parameters, and (IV) director instructions corresponding to close-up and/or mid-shot and/or animation;
linking said scene to another scene via a link, wherein the link is either included in the scene description or is kept in a separate file.

11. The method of claim 10, wherein said linking is conditional linking;
wherein a source scene links to either a first target scene if a parameter has a first value, or to a second target scene if said parameter has a second value,
thereby creating a dynamic script that procures a different set of scenes based on parameters that it receives.

12. The method of claim 10, comprising:
adding parameters for said scene to said scene description;

wherein the parameters are provided to a dynamic script from an ordering user by populating a form and filling in said parameters, wherein the parameters are fed into the dynamic script and the dynamic script evaluates a linear sequential order of scenes that compose an end-video to be displayed for a user.

13. The method of claim 12, comprising:
compiling a description of the dynamic script into a native programming language;
before or during said compiling, inserting a section that produces calculated variables that are parameters which depend on parameters that an ordering user provides.

14. The method of claim 13, wherein the method automatically produces a first video variant if a user-gender parameter indicates that the user is a male, and the method automatically produces a second video variant if the user-gender parameter indicates that the user is a female.

15. The method of claim 1, comprising:
providing instructions about medication to be taken by a viewer, by including in a video an image of the medication and a verbal description of the medication;
wherein the image is selected from a database of photographs;
wherein the image is sourced from an official medical source or from a manufacturer of the medication;
wherein, if the image data is structured, then image data is analyzed and converted into a format for a database that can be accessed by a video construction server;
wherein, if the image data is provided in free text and is meant for human consumption, then relevant information is extracted by using text processing techniques and/or Natural Language Processing (NLP), and the information is then interpreted and loaded into the database;
wherein extracted information from all sources is loaded into the database, and contents from all sources are merged to make an entire data set available;
utilizing the information to automatically produce rich media content, such that the output file includes up-to-date information;
wherein differences between older and newer data sets are determined to apply customizations or improvements to produced videos, wherein the differences are used to evaluate required changes to videos.

16. The method of claim 1, comprising:
providing instructions about medication to be taken by a viewer, by including in a video an image of the medication and a verbal description of the medication;
wherein the method comprises producing either two-dimensional or three-dimensional image of the medication, to enable the viewer to validate that a medication he is taking is the medication to which reference is made in the video;
wherein the method comprises:
(a) reading from a database a set of pill properties, wherein the pill properties are selected from the group consisting of: shape, color, size, score, and inscription;
(b) using said pill properties to define and render an image of a pill, wherein a produced image of the pill matches said pill properties, wherein the image is created without an actual image of the pill through an approximation so that the viewer can confirm that he has the proper pill;
(c) integrating the produced image of the pill to produce a video describing the actual pill, by rendering the produced image of the pill into a movie clip along with a soundtrack vocally describing the pill; wherein the movie clip is produced by taking the produced image of the pill and repeating it to produce said movie clip while adding a channel providing audio describing the pill.

17. A non-transitory storage medium having stored thereon instructions that, when executed by a hardware processor, cause the hardware processor to perform a method comprising:
(a) accepting (I) an ordered list of video input files intended for being chained together, and (II) a single output video file name;
(b) checking that all of said video input files match each other by having same encoding, same format, and same codec;
(c) creating an output file using a chosen container which matches, by its encoding and format and codec, a container of said video input files;
(d) sequentially opening each of said video input files;
(e) reading each packet from each video input file, without packet decoding, wherein each video input file comprises video packets;
(f) if the packet is a video packet, then writing the packet as-is to a video stream of the output file;
(g) if the packet is an audio packet, then writing the packet as-is to an audio stream of the output file;
(h) tracking the DTS timestamp value and the PTS timestamp value of each audio packet and each video packet, to keep all streams synchronized after completion of processing of each video input file;
(i) ensuring continued synchronization of multiple joined video input files by adjusting both the audio and the video to have the exact same duration, by performing one of:
(A) selecting the later timestamp from all the video input streams for resynchronization, by performing either: (I) adding a quiet audio delay, or (II) postponing the starting video frame for the next video input file in sequence;
(B) calculating an optimal time period based on lengths of the video input files and their sampling rates and codec types; wherein the optimal time period corresponds to a number of complete audio and video frames that start together and end together exactly within said optimal period; and adjusting each video input file so that its length conforms to an exact multiple of the optimal time period as above; and removing additional frames from the video input files either manually or automatically;
wherein step (i) is performed by determining a common synchronization period T for (I) encoded video that is saved at F frames per second, and (II) encoded audio that is sampled at S samples per second, wherein each audio frame has L samples,
wherein the common synchronization period is calculated by using the following equations, $T = V \times 1/F = A \times L/S$ by determining the minimum integer values of parameter A and parameter V such that the following condition holds true:

$V \times S = A \times F \times L$.

* * * * *